United States Patent [19]

Dorfeld et al.

[11] Patent Number: 5,785,726

[45] Date of Patent: Jul. 28, 1998

[54] METHOD OF REDUCING BUBBLES AT THE VESSEL/GLASS INTERFACE IN A GLASS MANUFACTURING SYSTEM

[75] Inventors: William G. Dorfeld, Beaver Dams; David M. Lineman, Painted Post, both of N.Y.

[73] Assignee: Corning Incorporated, Corning, N.Y.

[21] Appl. No.: 736,848

[22] Filed: Oct. 28, 1996

[51] Int. Cl.[6] .............................. C03B 5/16; C03B 5/18
[52] U.S. Cl. ................. 65/134.1; 65/134.2; 65/134.9; 65/157; 65/374.12
[58] Field of Search .............................. 65/134.1, 134.2, 65/134.5, 134.9, 157, 160, 335, 347, 374.12

[56] References Cited

U.S. PATENT DOCUMENTS

| | | | |
|---|---|---|---|
| 2,009,764 | 7/1935 | Dalton | 106/36.1 |
| 2,982,053 | 11/1961 | Elmer | 49/79 |
| 3,233,993 | 2/1966 | Weidel | 65/178 |
| 3,338,696 | 8/1967 | Dockerty | 65/145 |
| 3,682,609 | 8/1972 | Dockerty | 65/83 |
| 3,850,602 | 11/1974 | Bruning | 65/18 |
| 3,954,656 | 5/1976 | Deeg et al. | 252/301.4 |
| 4,704,153 | 11/1987 | Schwenninger et al. | 65/134 |
| 4,738,938 | 4/1988 | Kunkle et al. | 501/72 |
| 4,983,198 | 1/1991 | Ogino | 65/32.5 |
| 5,509,951 | 4/1996 | Baucke et al. | 65/134.6 |
| 5,688,300 | 11/1997 | Ashley et al. | 65/86 |

FOREIGN PATENT DOCUMENTS

| | | |
|---|---|---|
| 0 556576 A1 | 8/1993 | European Pat. Off. . |
| 0 607 865 A1 | 7/1994 | European Pat. Off. . |
| 92408 | 11/1968 | France . |
| 2221129 | 9/1990 | Japan . |
| 1147830 | 4/1969 | United Kingdom . |
| 83/00685 | 3/1983 | WIPO . |

OTHER PUBLICATIONS

Ebba de kever and Gunther Heinz Frischat. "Influence of batch moisture and atmosphere on the melting behavior of $As_2O_3$–and $Sb_2O_3$–containing glasses", Glastechnische Berichte, Feb. 1992, pp. 64–66.

Edith M. Firth, F.W. Hodkin, Michael Parkin, W.E.S. Turner, "The Effect of Moisture on the Melting, Working, and other Properties of Totash–Lead Oxide–Silica Glasses of the 'English Crystal' Type", Journal of the Society of Glass Technology, 1926, vol. X., pp. 220–229.

S.M. Budd, V.H. Exelby and J.J. Kirwan, "The Formation of Gas Bubbles in Glass at High Temperature", Glass Technology vol. 3 No. 4 Aug. 1962, pp. 124–129.

M. Boffe, G. Percriaux and E. Plumat, "Formation of Bubbles During Devitrification and Remelting of Crystals in Glass", Nucleation and Crystallization Symposium, pp. 47–54.

J.E. Fenstermacher, R.C. Lesser and R.J. Ryder, "A Study of Water Content of Container Glasses", The Glass Industry/Sep. 1965, pp. 518–521.

Dr. J.P. Poole, "Fundamentals of Fining", Commission on Glass, Annual Meeting, Toronto, Canada, 1969, pp. 169–176.

Dr. Horst Scholze, "Gases and Water in Glass", Part one, Lectures on Glass and Technology, Rensselaer Polytechnic Institute, Troy, NY, Mar. 30–Apr. 1, 1996. 19 pages.

Robert J. Eagan and Gary J. Jones, "Bubble Formation in Glass by Reaction with Silicon and Silicon–Germanium Alloys", Sep. 2, 1992. pp. 300–301.

Primary Examiner—Peter Chin
Assistant Examiner—Jacqueline A. Ruller
Attorney, Agent, or Firm—Robert L. Carlson

[57] ABSTRACT

A method of making glasses with manufacturing systems employing platinum or molybdenum melting, fining delivery, or forming vessel, wherein the partial pressure of hydrogen outside the vessel is controlled or manipulated, relative to the partial pressure of hydrogen inside the platinum structure, to minimize surface blistering in the glass in contact with the platinum or molybdenum.

25 Claims, 1 Drawing Sheet

METHOD OF REDUCING BUBBLES AT THE VESSEL/GLASS INTERFACE IN A GLASS MANUFACTURING SYSTEM

FIELD OF THE INVENTION

This invention is directed to a method of forming glasses, particularly those which are relatively arsenic-free, in manufacturing systems which employ platinum or molybdenum. The invention is particularly useful for forming high melting or high strain point glasses, e.g. such as are used for glass substrates for flat panel display devices, without having to use such arsenic containing materials.

BACKGROUND OF THE INVENTION

Liquid crystal displays (LCDs) are passive flat panel displays which depend upon external sources of light for illumination. They are manufactured as segmented displays or in one of two basic configurations. The substrate needs (other than being transparent and capable of withstanding the chemical conditions to which it is exposed during display processing) of the two matrix types vary. The first type is intrinsic matrix addressed, relying upon the threshold properties of the liquid crystal material. The second is extrinsic matrix or active matrix (AM) addressed, in which an array of diodes, metal-insulator-metal (MIM) devices, or thin film transistors (TFTs) supplies an electronic switch to each pixel. In both cases, two sheets of glass form the structure of the display. The separation between the two sheets is the critical gap dimension, of the order of 5–10 µm.

Intrinsically addressed LCDs are fabricated using metal deposition techniques, typically at temperatures ≦350° C., followed by standard metal etching procedures. As a result, the substrate requirements therefor are often the same as those for segmented displays. Soda-lime-silica glass with a barrier layer has proven to be adequate for most needs. A high performance version of intrinsically addressed LCDs, the super twisted nematic (STN) type, has an added requirement of extremely precise flatness for the purpose of holding the gap dimensions uniform. Because of that requirement, soda-lime-silica glass made using the float glass manufacturing process must be polished. Such polishing processes are expensive and time consuming, and generate a large amount of glass particles which have the potential to negatively impact further processing of the glass sheets. Alternatively, glass can be formed using a process which does not require polishing, e.g. fusion downdraw.

Extrinsically addressed LCD's can be further subdivided depending upon the nature of the electrical switch located at each optical element (subpixel). Two of the most popular types of extrinsically (or active matrix, AMLCD) addressed LCD's are those based on either amorphous (a-Si) or polycrystalline (poly-Si) silicon thin film transistors (TFT's).

U.S. Pat. No. 4,824,808 (Dumbaugh, Jr.) lists four desirable properties for a glass to exhibit in order to fully satisfy the needs of a substrate for extrinsically addressed LCD's:

First, the glass must be essentially free of intentionally added alkali metal oxide to avoid the possibility of alkali metal contamination of the TFT;

Second, the glass substrate must be sufficiently chemically durable to withstand the reagents used during the manufacture of the TFT;

Third, the expansion mismatch between the glass and the silicon present in the TFT array must be maintained at a relatively low level even as processing temperatures for the substrates increase; and Fourth, the glass must be capable of being produced in high quality thin sheet form at low cost; that is, it must not require extensive grinding and polishing to secure the necessary surface finish.

That last requirement is most difficult to achieve inasmuch as it demands a sheet glass production process capable of producing essentially finished glass sheet. A process capable of meeting this requirement is a particular downdraw process known as the overflow downdraw, or fusion, sheet manufacturing process. The overflow downdraw process is described, for example, in U.S. Pat. No. 3,338,696 (Dockerty) and U.S. Pat. No. 3,682,609 (Dockerty). Fusion formed glass sheets, unlike float glass sheets, are sufficiently flat that they do not need to be polished after forming. Two glasses which meet the above requirements, Corning Incorporated Codes 7059 and 1737 sheet glass, are currently employed as substrates for extrinsically addressed LCD's. These glasses are made using the overflow downdraw process, and hence do not require polishing after forming.

Recent improvements in the resolution of extrinsically addressed LCD's have led to the development of a fifth glass requirement, that is, a high glass strain point. As can be appreciated, the higher the strain point, the greater the resistance to thermal shrinkage. Low thermal shrinkage is desirable for precise alignment during successive photolithographic and other patterning steps during the TFT processing. Consequently, glasses having higher strain points are generally preferred for extrinsically addressed LCD's, particularly those which employ poly-Si TFT technology. Thus, there has been considerable research to develop glasses demonstrating high strain points so that thermal shrinkage is minimized during device processing. Corning Code 1737 glass, which has the highest strain point (666° C.) in the AMLCD substrate industry, is rapidly becoming an industry standard. Concurrent with their high strain points, these glasses often have high melting temperatures, e.g. on the order of 1550°–1650° C.

Another technology termed "chip-on-glass" (COG) has further emphasized the need for the substrate glass to closely match silicon in thermal expansion. Thus, the initial LCD devices did not have their driver chips mounted on the substrate glass. Instead, the silicon chips were mounted remotely and were connected to the LCD substrate circuitry with compliant or flexible wiring. As LCD device technology improved and as the devices became larger and required finer resolutions, these flexible mountings became unacceptable, both because of cost and of uncertain reliability. This situation led to Tape Automatic Bonding (TAB) of the silicon chips. In that process the silicon chips and electrical connections to the chips were mounted on a carrier tape, that subassembly was mounted directly on the LCD substrate, and thereafter the connection to the LCD circuitry was completed. TAB decreased cost while improving reliability and increasing the permitted density of the conductors to a pitch of approximately 200 µm—all significant factors. COG, however, provides further improvement over TAB with respect to those three factors. Hence, as the size and quality requirements of LCD devices increase, COG is demanded for those devices dependent upon the use of integrated circuit silicon chips. For that reason, the substrate glass preferably demonstrate a linear coefficient of thermal expansion closely matching that of silicon; i.e., a linear coefficient of thermal expansion (0°–300° C.) between about 32–46×10$^{-7}$/°C. most preferably 32–40×10$^{-7}$/°C.

Many of the glasses manufactured for flat panel display applications, particularly those which are formed by downdraw processes (e.g., the fusion or slot draw processes), are melted or formed using manufacturing equipment comprised of refractory metals, e.g. platinum or platinum alloys. This is particularly true in the fining and conditioning sections of the process, where refractory metals are employed in order to minimize the creation of compositional inhomogeneities and gaseous inclusions caused by contact of the glass with oxide refractory materials. In addition, many of these manufacturing processes employ arsenic as a fining agent. This is because arsenic is among the highest temperature fining agents known, meaning that, when added to the molten glass bath, it allows for $O_2$ release from the glass melt even at high melting temperatures (e.g. above 1450° C.). This high temperature $O_2$ release (which aids in the removal of bubbles during the melting and fining stages of glass production), coupled with a strong tendency for $O_2$ absorption at lower conditioning temperatures (which aids in the collapse of any residual gaseous inclusions in the glass), results in a glass product essentially free of gaseous inclusions. Other fining agents typically melt and release their oxygen far too early when added as fining agents to high melting temperature glasses and reabsorb $O_2$ too late during the conditioning process, thereby disabling their fining and oxygen reabsorption abilities.

From an environmental point of view, it would be desirable to find alternative methods of making such high melting point and strain point glasses without having to employ arsenic as a fining agent. It would be particularly desirable to find methods for making such glasses via downdraw (especially fusion-like) processes. Unfortunately, previous efforts at doing so have been hindered by the production of unacceptable amounts of bubbles in the glass. This has been a particular problem with glasses which employ refractory metals such as platinum or platinum containing alloys in their molten glass delivery systems. This is because metals such as platinum (and molybdenum) can cause an electrochemical reaction to occur with the glass which results in bubble formation at the glass/platinum (or glass/molybdenum) interface, i.e. where the glass contacts the platinum. This bubble formation in the glass/platinum or glass/molybdenum contact regions is referred to herein as surface blistering.

SUMMARY OF THE INVENTION

The present invention relates to a method of forming glasses in manufacturing processes which employ platinum, palladium, rhodium, molybdenum, or alloys thereof in the melting, fining, delivery, conditioning or forming sections of the manufacturing process. The present invention involves control of the partial pressure of hydrogen outside the pertinent manufacturing vessel relative to the partial pressure of hydrogen in the glass or inside that manufacturing vessel. By so controlling the relative partial pressures of hydrogen inside versus outside the platinum or molybdenum containing portion of the glass manufacturing system, we can control, and if desired, reduce the amount of surface blisters which were heretofore problematic in such glass manufacturing systems which employed platinum or molybdenum. The partial vapor pressure of hydrogen inside and outside the system can be controlled, for example, by controlling the partial vapor pressure of water inside and outside the system.

For glass manufacturing systems which employ platinum containing forming vessels, for example, we have found that by adjusting the partial vapor pressure of water (and thus the partial vapor pressure of hydrogen) outside the platinum forming vessel relative to the partial vapor pressure of water (and thus the partial vapor pressure of hydrogen) in the molten glass, or inside the forming vessel, glasses may be successfully fined without having to use $As_2O_3$. If needed or desired, other fining constituents which are normally less efficient than $As_2O_3$ at high melting temperatures (melting temperature is defined herein as the temperature at which the glass exhibits a viscosity of 200 poise) may be used successfully. Examples of such fining agents include $Sb_2O_3$, $CeO_2$, $SnO_2$, $Fe_2O_3$,halides, sulfates, and mixtures thereof. Such fining agents can be employed in place of $As_2O_3$ in accordance with the present invention to successfully fine the glass in glass manufacturing systems which employ platinum or molybdenum manufacturing vessels.

The desired relationship between the inner and outer hydrogen partial vapor pressures may be facilitated, for example, by employing a relatively low water content in the glass during the melting, fining, conditioning, delivery and forming processes. Alternatively, in accordance with the present invention, such a relationship can be facilitated by controlling the atmosphere outside the platinum-containing or molybdenum containing manufacturing vessel. Platinum or molybdenum containing manufacturing vessel, as used herein, means a component in the manufacturing process which is located prior to the point at which the glass reaches its final shape and which employs platinum or molybdenum in contacting relationship with the glass (thus, a manufacturing system which employs platinum or molybdenum in its melting, fining, conditioning, delivery tubes, or forming sections).

Control of the atmosphere around the platinum or molybdenum containing vessel is facilitated, for example, by building an atmosphere controlling enclosure around the platinum (or molybdenum) containing portion of the process. Alternatively, a larger enclosure can be provided around the entire manufacturing process or otherwise an ambient air atmosphere can be provided in which the dew point of the air atmosphere is controlled so that the partial vapor pressure of water (and hence hydrogen) outside the forming process is controlled compared to that present inside the forming process.

The present invention is believed to be applicable to the formation of any oxide glass which is made using a manufacturing process employing a platinum or molybdenum manufacturing vessel. The invention is particularly useful for making borosilicate and aluminosilicate glasses, particularly those which have melting points (defined herein as the temperature in which the viscosity corresponds to 200 poise) greater than about 1500° C., as well as glasses having high strain points, i.e, greater than 630° C., more preferably greater than 640° C. Such glasses heretofore were typically made using considerable amounts of $As_2O_3$ as a fining agent. The present invention enables the formation of such high melting point and high strain point glasses which are essentially or substantially arsenic-free. By substantially arsenic-free it is meant that such glasses have less than 0.02 mole percent $As_2O_3$ (such amounts are normally present as a result of raw material impurity). This is a significant achievement which can immediately be employed in a number of technologies, one in particular being the formation of high strain point glass sheet substrates for flat panel displays. The invention also enables the formation of such high melting point glasses using manufacturing systems which employ platinum or molybdenum or alloys thereof which contact the glass during the melting or forming steps of the manufacturing process. This process is particularly suited for forming glasses which are formed using a downdraw process. The methods of the present invention enable the formation of other high strain point (i.e., greater than about 630° C.) silicate glasses, particularly aluminosilicate and borosilicate glasses, while requiring little or no arsenic as a fining agent.

The desired relative partial pressures inside versus outside the forming vessels depends upon whether the forming vessel contains platinum or molybdenum (or palladium or rhodium) as a glass contacting material.

For example, platinum is desirable for use in glass forming vessels primarily because of its inert properties. However, platinum enables hydrogen migration to occur from the glass melt through the platinum, thereby creating an oxygen rich layer at the glass/platinum interface which results in surface blisters. Consequently, for the platinum glass manufacturing vessels, it is most desirable to maintain the relative inside and outside partial pressures of hydrogen to be substantially equal, so that no migration of hydrogen, either in or out of the glass manufacturing vessel, occurs. However, if any migration is to occur, it is more desirable that it occur from the outside in, and thus in another embodiment the partial pressure of hydrogen outside the platinum or molybdenum manufacturing vessel is maintained at a higher level then is present inside the vessel.

On the other hand, molybdenum acts as a reducing material toward oxide melts. Therefore it is desirable to maintain a partial pressure of hydrogen outside the molybdenum containing forming vessel which is lower than that inside the forming vessel, to reduce the amount of blisters formed as a result of reduction of the glass constituents (e.g. formation of $SO_2$ bubbles as a result of reduction of dissolved $SO_3$).

DETAILED DESCRIPTION OF THE INVENTION

Figure 1:
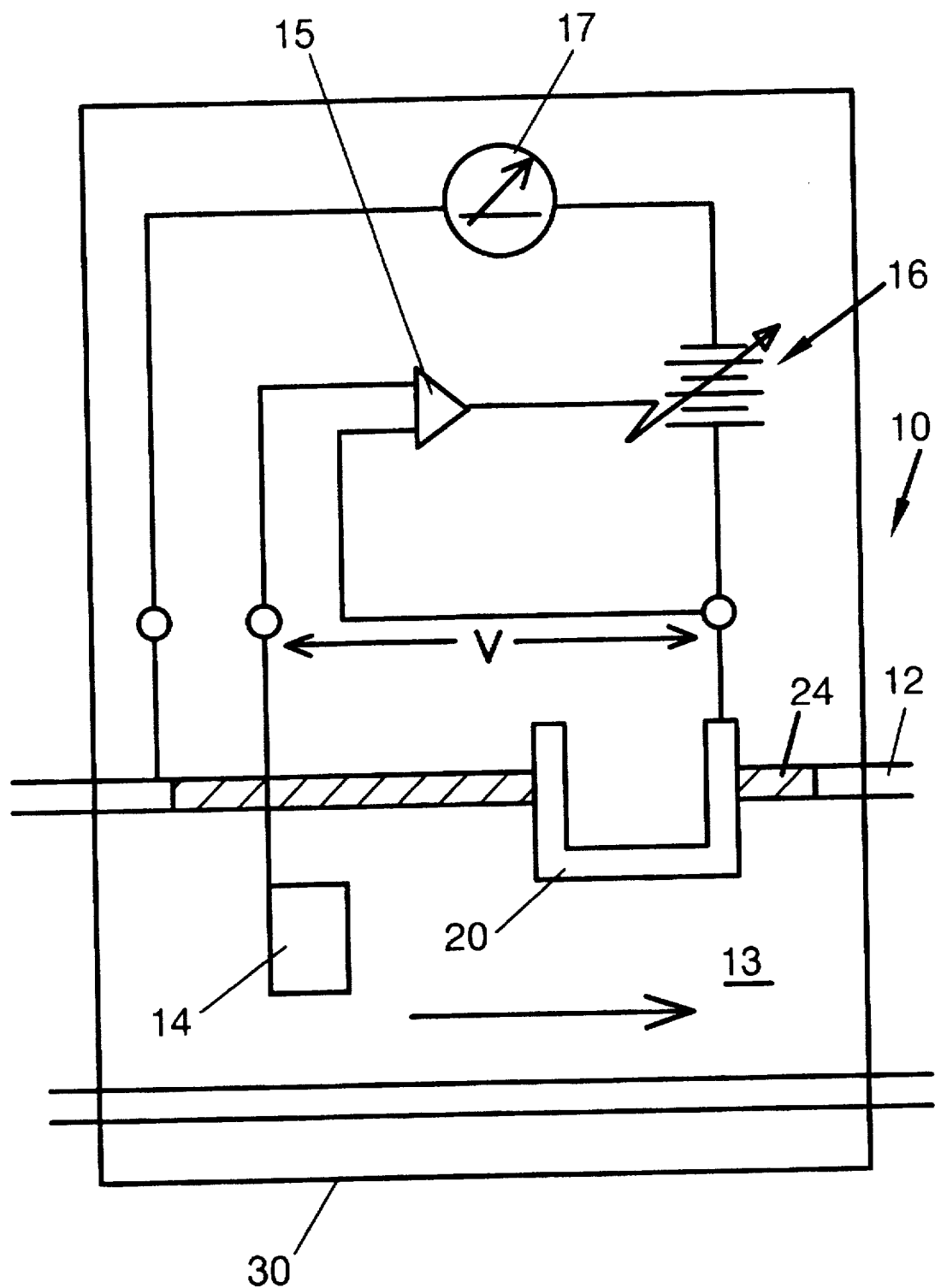
FIG. 1 illustrates a humidity controlled enclosure in accordance with the present invention.

The present invention relates to a method of melting and forming glasses in platinum or molybdenum containing manufacturing systems. The present invention makes forming of glasses, even high melting point (greater than about 1500° C.) silicate glass compositions, possible without having to employ substantial amounts of arsenic as a fining agent. While not wishing to be bound by theory, it is believed that the bubble forming surface blistering effect which occurs in platinum systems, for example, occurs as a result of formation of an oxygen rich layer near the platinum-glass melt interface. This oxygen rich layer in the glass is believed to be produced by a combination of thermoelectric electrolysis of the melt, breakdown of oxide fining agents, and the number of OH groups dissolved in the glass. The latter effect is believed to have a large impact on the rate of blistering as a result of contact of the glass with the platinum. It is believed that OH groups dissociate into neutral hydrogen and oxygen. The hydrogen can then permeate the platinum skin, enriching the surface region (platinum contacting region) of the glass with oxygen which can then form bubbles if the solubility limit of the glass is exceeded. Thus, by controlling the relative partial pressures of hydrogen outside the system versus those inside the system, hydrogen permeation through the platinum metal can be controlled, so that bubble generation is reduced.

This can be achieved, for example, by controlling the amount of water (and thus the partial vapor pressure of hydrogen), in the air surrounding the platinum vessel. To facilitate formation of the latter, the platinum containing portion of the manufacturing system could be enclosed, for example, in a humidity jacket in which the partial pressure of water is controlled as a means to producing a controlled high partial pressure of hydrogen to counter diffusion of hydrogen from the glass through the platinum and into the atmosphere (as in the case of platinum vessels). This would remove a significant contributor to the oxidized boundary layer in the platinum system and could act in addition to reduce any excess oxidation by converting dissolved $O_2$ to OH groups in the glass melt. The overall impact is to minimize oxygen blister formation in the melting and forming sections of the manufacturing process which employ platinum.

It is believed that the configuration of the humidity jacket or enclosure is not critical. It should be relatively leak tight but as its function is to maintain a partial pressure of water rather than exclude a gas, vacuum tightness is not required. A positive pressure is preferably employed within the enclosure so that air from the atmosphere outside the enclosure is not introduced into the inside of the enclosure. For platinum containing systems, it is desirable to maintain as high a partial pressure of water as possible. The upper limit of this partial pressure, and thus the controlled dew point, depends on a number of factors, including the particular glass being melted, the fining agents employed, and whether the manufacturing systems employ molybdenum and/or platinum. For example, for the Example 3 glass composition set forth in Table I below, it is currently believed that a controlled dew point between about 55° and 65° F. would be most desirable to avoid blisters. Some heating is expected simply by enclosing the high temperature section of the manufacturing process which employs platinum metal, and thus additional heating of the enclosure may or may not be necessary. Water vapor can be introduced, for example, by employing common techniques used in humidifiers, or boiling or flash vaporizing a control flow of water, if needed or desired. In an alternative embodiment, hydrogen gas could be employed to control the hydrogen partial pressure, e.g. a mixture of primarily nitrogen gas, with a percentage of hydrogen gas mixed in, could be pumped into the enclosure, the percentage of hydrogen being varied as desired.

The present invention also relates to silicate glass compositions and methods of making such silicate glass compositions while employing little or no arsenic. The preferred glasses are aluminosilicate or borosilicate glasses. The preferred manufacturing processes for such glasses is via a downdraw sheet manufacturing process. As used herein, downdraw sheet manufacturing process refers to any form of glass sheet manufacturing process in which glass sheets are formed while traveling in a downward direction. In the fusion or overflow downdraw forming process, molten glass flows into a trough, then overflows and runs down both sides of a pipe, fusing together at what is known as the root (where the pipe ends and the two overflow portions of glass rejoin), and is drawn downward until cool. The overflow downdraw sheet manufacturing process is described, for example, in U.S. Pat. No. 3,338,696 (Dockerty) and U.S. Pat. No. 3,682,609 (Dockerty). One advantage to the fusion forming process is that the glass sheet can be formed without the glass surface contacting any refractory forming surfaces. This provides for a smooth, contaminant-free surface. In addition, this technique is capable of forming very flat and thin sheets to very high tolerances. Consequently, fusion formed glass sheets, unlike float glass sheets, do not require costly polishing steps for TFT and STN LCD applications.

Other forms of downdraw sheet forming techniques include the slot draw and redraw forming techniques. In the slot draw technique, molten glass flows into a trough having a machined slot in the bottom. The sheets of glass are pulled down through the slot. The quality of the glass is obviously dependent on the accuracy of the machined slot. Redraw processes generally involve preforming a glass composition into a block of some shape, then reheating and drawing the glass downwardly into a thinner sheet product.

In a preferred embodiment, the water content in the glass being formed is maintained at a relatively low level. One manner of measuring the water content in the glass is by measuring beta-OH (β-OH). β-OH, as used herein, is a measure of the hydroxyl content in the glass as measured by IR spectroscopy, and is determined using the fundamental hydroxyl absorption, which for this material occurs at about 2800 nm. The β-OH is the linear absorption coefficient (absorbance/mm thickness) of the material at 2809 nm. The equation below shows how β-OH is calculated from the sample's IR transmittance spectrum.

$$\beta\text{-OH}=(1/X)\ \text{LOG}_{10}(T_1/T_2)$$

where X is the sample thickness in millimeters, $T_1$ is the sample transmittance at the reference wavelength (2600 nm) and $T_2$ is the minimum sample transmittance of the hydroxyl absorption wavelength (2809 nm). The reference wavelength compensates for signal loss due to surface reflections, scatter, and refraction in the sample, and is chosen from a region of no absorption and as close as possible to the absorption wavelength of interest.

In a preferred embodiment of the present invention for forming low arsenic containing glasses via a downdraw sheet forming process, the batch constituents are selected so that the resultant glass has a water content therein, as indicated by β-OH level, which is less than 0.5, more preferably less than 0.4, and most preferably less than 0.35.

Preferably, the glasses formed in accordance with the invention contain less than 0.1 mole percent $As_2O_3$, and most preferably are essentially free of $As_2O_3$. We have found that using the methods of the present invention, silicate glasses (especially aluminosilicate and borosilicate glasses) can be formed using less than 0.05 mole percent $As_2O_3$, and even less than 0.02 mole percent $As_2O_3$, expressed as the amount of $As_2O_3$ present in the resultant glass. Even when formed using a downdraw sheet forming process employing a platinum based metal delivery system, such glasses can be formed without any significant amounts of electrochemical blistering occurring. In the most preferred embodiment, in order to facilitate fining of these glasses, $Sb_2O_3$, $CeO_2$, $SnO_2$, $Fe_2O_3$, and mixtures thereof are added to such glasses, alone or in combination, in an amount between about 0.02–2 mole percent. In a preferred embodiment, $Sb_2O_3$ is added in an amount between about 0.2–0.5 mole percent.

The water content or β-OH value of the glass can be reduced in a variety of ways. For example, simply by appropriate selection of batch materials, the water level in the glass can be adjusted to some extent. Further water reduction can be achieved by adding drying agents, such as halide materials. For example, halide containing materials may be added in an amount which results in the final glass having a composition between about 0.1 to 4 mole percent halide, more preferably 0.1 to 2 mole percent halide, and most preferably about 0.1 to 0.3 mole percent halide. In a preferred embodiment for forming the glass composition disclosed in the example, 0.4 mole percent chlorine is batched, e.g. as $CaCl_2$, resulting in about 0.15 to 0.19 mole percent Cl in the resultant glass.

Additionally, it is desirable to keep the sum of the partial pressures of all volatile gases dissolved in the glass below 1 atmosphere. One method of facilitating this result is by limiting the amount of sulfur in the resultant glass by appropriate selection of batch materials. Preferably, selection of batch materials should be made so that the sulfur, expressed as $SO_3$, in the resultant formed glass is as low as possible, preferably less than 100 ppm, more preferably less than 50, and most preferably less than 25 ppm.

The methods in accordance with the present invention are particularly advantageous in forming high strain point aluminoborosilicate glasses such as, for example, those having a composition, expressed in terms of mole percent on the oxide basis, of

| | |
|---|---|
| $SiO_2$ | 60–73 |
| $Al_2O_3$ | 8–14 |
| $B_2O_3$ | 5–17 |
| $TiO_2$ | 0–5 |
| $Ta_2O_5$ | 0–5 |
| MgO | 0–5 |
| CaO | 1–13 |
| SrO | 0–8 |
| BaO | 0–14 |

More preferably, the base glass has a composition, expressed in terms of mole percent on the oxide basis, of

| | |
|---|---|
| $SiO_2$ | 64–70 |
| $Al_2O_3$ | 9.5–14 |
| $B_2O_3$ | 5–12 |
| $TiO_2$ | 0–5 |
| $Ta_2O_5$ | 0–5 |
| MgO | 0–5 |
| CaO | 3–13 |
| SrO | 0–5.5 |
| BaO | 2–8 |
| MgO + CaO + SrO + BaO | 10–20. |

Glasses within this preferred composition range are disclosed, for example, in U.S. Pat. No. 5,374,595, the specification of which is hereby incorporated by reference. Preferred glasses formed in accordance with the present invention exhibit linear coefficients of thermal expansion over the temperature range of 0°–300° C. between 32–46× $10^{-7}$/°C., more preferably between 32–40×$10^{-7}$/°C.; strain points higher than 630° C., more preferably higher than 640° C., and most preferably greater than 650° C.; liquidus temperatures less than 1125° C.; liquidus viscosities which are sufficient to enable formation by a downdraw manufacturing process, preferably greater than 400,000, and more preferably greater than 600,000 poises (60,000 Pa-s); a weight loss of less than 2 mg/cm² after immersion for 24 hours in an aqueous 5% by weight HCl solution at 95° C.; long term stability against devitrification at melting and forming temperatures, and melting viscosities of about 200 poises (20 Pa.s) at less than 1675° C. The methods of the present invention may be employed in glasses having compositions within the boundaries set forth above, such as, for example, glasses listed as examples in U.S. Pat. No. 5,374, 595, thereby enabling such glasses to be fined and formed without having to use arsenic.

In the most preferred glasses, in addition to the low water level, the level of $Al_2O_3$ will exceed that of $B_2O_3$ and in the most preferred glasses the composition will consist essentially, expressed in terms of mole percent, of about

| | |
|---|---|
| SiO$_2$ | 65–69 |
| Al$_2$O$_3$ | 10–12 |
| B$_2$O$_3$ | 7–10 |
| TiO$_2$ | 0–3 |
| Ta$_2$O$_5$ | 0–3 |
| MgO | 1–5 |
| CaO | 3–9 |
| SrO | 1–3 |
| BaO | 2–5 |
| MgO + CaO + SrO + BaO | 11–16 |

Preferably, the ratio Al$_2$O$_3$:B$_2$O$_3$ in such glasses is greater than 1.

The glasses of the present invention preferably have less than 0.2 mole percent As$_2$O$_3$, more preferably less than 0.05 mole percent As$_2$O$_3$, and most preferably less than 0.02 mole percent As$_2$O$_3$ (an amount which is normally present as a result of raw material impurity). Such glasses are also described in U.S. patent application Ser. No. 08/742,610 filed simultaneously herewith, the specification of which is hereby incorporated by reference.

It is believed that the methods described herein are applicable to a wide variety of glasses, particularly those formed via downdraw manufacturing processes which employ platinum in their forming regions. For example, while not limited thereto, application of the invention is believed to be beneficial to forming glasses such as those set forth in Table I below. These glasses were prepared in a laboratory-scaled continuous melting unit similar to the overflow downdraw melting units typically used for commercial production of this type of product. This experimental melting unit employs a platinum/rhodium alloy refractory metal delivery system, wherein the molten glass contacts the platinum alloy metal. Example 4 of Table I corresponds closely to commercially available Corning Code 1737 glass, and was fined accordingly using an amount of arsenic which resulted in about 0.4 mole percent being present in the resultant glass. Examples 1, 2, and 3 illustrate the effect that decreasing amounts of water has on these compositions. As the β-OH values of the glass decrease, so do the gaseous inclusions (Inc./lb.) in glass. In these examples, gaseous inclusions are primarily a result of electrochemical blistering caused by the platinum alloy pipes which deliver the molten glass, and consequently accurately mimic the manufacturing processes employing metals such as platinum. Gaseous inclusions were measured on a per pound basis over a period of two to three days. As illustrated by the examples, the inclusions per pound dropped significantly with each decrease of β-OH value. The fact that this was done without having to use As$_2$O$_3$ as a fining agent makes this accomplishment significant.

Table I records similar glass compositions of varying β-OH levels, expressed in terms of parts by weight on the oxide basis, illustrating the invention. Inasmuch as the sum of the individual constituents totals or very closely approximates 100, for all practical purposes the reported values may be deemed to represent weight percent. Table IA records the same glass compositions expressed in terms of mole percent on the oxide basis. The actual batch ingredients may comprise any materials, either oxides or other compounds, which, when melted together with the other batch components, will be converted into the desired oxide in the proper proportions. For example, SrCO$_3$ and CaCO$_3$ can provide the source of SrO and CaO, respectively. In Example 3, Cl was added as CaCl$_2$ at a level of 0.2 weight percent in excess of the batch, resulting in about 0.087 weight percent Cl retained in the resultant glass. About 2.7 weight percent water in excess of the batch was added to Examples 1 and 4.

Table I also lists measurements of several chemical and physical properties determined on the glasses in accordance with techniques conventional in the glass art. Thus, the linear coefficient of thermal expansion (CTE) over the temperature range 0°–300° C. expressed in terms of X10$^{-7}$/°C., and the softening point (S.P.), annealing point (A.P.), and strain point (St.P.) expressed in terms of °C., were determined by fiber elongation. The durability (HCl Dur.) in HCl was determined by measuring the weight loss (mg/cm$^2$) after immersion in a bath of aqueous 5% by weight HCl at 95° C. for 24 hours.

The liquidus temperatures (Liq.Temp.) of the glasses were measured using the standard liquidus method, which involves placing crushed glass particles in a platinum boat, placing the boat in a furnace having a region of gradient temperatures, heating the boat in an appropriate temperature region for 24 hours, and determining by means of microscopic examination the highest temperature at which crystals appear in the interior of the glass. The melting temperature (M.P., in °C.) (defined as the temperature at which the glass melt demonstrates a viscosity of 200 poises [20 Pa.s]) was calculated employing the Fulcher equation as fit to the high temperature viscosity data. The liquidus viscosity (Liq. Vis.) was also calculated using the Fulcher equation coefficients, and is expressed in terms of X1,000,000 poises (100,000 Pa.s). SnO$_2$ was added to examples 1–3 in an amount suitable to replicate melting conditions in production, wherein the tin electrodes employed in melting the glass result in residual tin oxide in the resultant glass.

TABLE I

| | 1 | 2 | 3 | 4 |
|---|---|---|---|---|
| SiO$_2$ | 59.49 | 58.82 | 58.91 | 57.07 |
| Al$_2$O$_3$ | 16.4 | 16.7 | 16.58 | 16.46 |
| B$_2$O$_3$ | 8.29 | 8.3 | 8.21 | 8.35 |
| MgO | 0.737 | 0.739 | 0.765 | 0.77 |
| CaO | 4.109 | 4.111 | 4.116 | 4.21 |
| SrO | 1.889 | 1.883 | 1.887 | 1.88 |
| BaO | 8.6 | 8.59 | 8.61 | 9.49 |
| SnO$_2$ | 0.062 | 0.09 | 0.092 | |
| Sb$_2$O$_3$ | 1.857 | 1.852 | 1.856 | 0 |
| As$_2$O$_3$ | 0 | 0 | 0 | 1.11 |
| % Added H$_2$O | 2.70 | 0 | 0 | 2.7 |
| Cl | 0 | 0 | 0.087 | 0 |
| β-OH | 0.481 | 0.41 | 0.358 | 0.440 |
| Inc./lb. | 15.2 | 2.06 | 0.26 | .21 |
| S.P. | 973 | 976 | 977 | 968 |
| M.P. | 1641 | 1638 | 1644 | 1625 |
| St. Pt. | 660 | 665 | 664 | 658 |
| A.P. | 717 | 719 | 720 | 714 |
| Liq. Temp. | 1080 | 1080 | 1090 | 1050 |
| Liq. Vis. | 1.37 | 1.4 | 1.06 | 2.51 |
| HCl Dur. | 0.46 | 0.44 | 0.45 | 0.61 |
| CTE | 36.3 | 36.6 | 36.6 | 37.6 |

TABLE IA

| | 1 | 2 | 3 | 4 |
|---|---|---|---|---|
| SiO$_2$ | 68.6 | 68.2 | 68.3 | 67.3 |
| Al$_2$O$_3$ | 11.1 | 11.4 | 11.3 | 11.4 |
| B$_2$O$_3$ | 8.25 | 8.31 | 8.22 | 8.5 |
| MgO | 1.27 | 1.28 | 1.32 | 1.35 |
| CaO | 5.08 | 5.11 | 5.11 | 5.32 |
| SrO | 1.26 | 1.27 | 1.27 | 1.28 |
| BaO | 3.89 | 3.9 | 3.91 | 4.39 |
| SnO$_2$ | 0.03 | 0.04 | 0.04 | — |
| Sb$_2$O$_3$ | 0.44 | 0.44 | 0.44 | — |
| As$_2$O$_3$ | | | | 0.4 |

The following example, which is meant to be illustrative and not limiting, demonstrates the effect that controlling the partial pressure of hydrogen outside a platinum forming, melting, or delivery system can have on the resultant glass.

EXAMPLE

This example illustrates that the dew point of the atmosphere on the air contact surface of the Pt vessel influences the $pO_2$ (the partial pressure of $O_2$) at the glass/Pt interface, and consequently the amount of oxygen surface blisters formed in this region. In this experiment, two closed end 0.435" diameter Pt-10Rh tubes with 0.030 inch thick walls were immersed into a molten glass having a composition similar to Ex. 3 above (thus, the glass was fined using $Sb_2O_3$) and heated to about 1590° C. Throughout the experiment the dew points in these two tubes were maintained at 68° and 87° F., respectively. Also immersed in the glass was a zirconia oxygen reference electrode, which was used as a stable reference electrode. The partial pressure of oxygen and the dew point inside the zirconia oxygen sensor was held constant. Such oxygen electrodes are not susceptible to hydrogen migration due to partial pressure differences, as is platinum, and therefore make a good reference electrode. The D.C. potential of each of the platinum tubes relative to the zirconia oxygen electrode was then monitored for 100 hours. The d.c. potential equilibrated in about 4 to 5 hours. After 100 hours, the experiment was terminated and samples of Pt from the glass exposure portion of the tubes taken for Sb analysis. We have found that the equilabrated DC potential measured is related to the partial pressure of oxygen in the glass melt at the tube surface through the Nernst equation. The numbers reported below for partial pressure of oxygen at the interface between the molten glass and the platinum tubes were thus calculated using the Nernst equation;

$E=(RT/nF) \ln(pO_2$ at the Pt/glass interface/$pO_2$ of reference), where:

R=Gas constant
T=Temperature in degrees K
n=# of electrons exchanged (4)
F=Faraday's constant.

The results from this test showed that the DC potential and hence the partial pressure of oxygen at the Pt/glass interface was related to the dew point of the atmosphere inside the platinum tube. The level of Sb contamination in the platinum was also related to the $pO_2$ at the Pt/glass interface.

| Dew Point | $pO_2$ | ppm Sb in Pt |
| --- | --- | --- |
| 68° F. | 0.48 atm | 337 |
| 87° F. | 0.19 atm | 623 |

This example demonstrates that, as the dew point decreased, the partial pressure of oxygen at the platinum/glass interface increased. The increased partial pressure of oxygen at the platinum/glass interface evidences a migration of hydrogen through the platinum into the outside atmosphere. If this were a glass manufacturing process, the resultant increase in partial vapor pressure of oxygen at the platinum/glass interface would result in increased blistering in this region. Also evident is the fact that as the dew point is increased the concentration of antimony (employed in this case as a fining agent) migrating into the platinum increased as well. This can be a problem as well, because as the amount of Sb increased in the Pt vessel, the melting point of the Pt/Sb alloy which results is generally lower than that of the Pt or Pt/Rh alloy which is typically employed. This can lead to obvious manufacturing problems, e.g. melting of the Pt-containing vessel. Consequently, for glasses which are fined using $Sb_2O_3$, the dew point outside the platinum vessel should preferably be maintained at a level where blister formation does not occur appreciably in the glass, and yet Sb migration into the platinum vessel is substantially minimized.

The optimum dew point for a given glass manufacturing process will vary depending on a variety of factors, including the particular manufacturing process and the glass composition being formed. In one manufacturing process, for example, a condition of zero net hydrogen migration through the Pt may be desirable. Under such conditions the precious metal container would approximate an inert vessel (i.e., no hydrogen migration would occur through the vessel walls).

In a preferred embodiment, the diffusive hydrogen flux is monitored by a sensing device. For example, such a sensing device may be similar to that described in the example above, in which a section of the platinum wall is isolated electrically from the main platinum vessel and its d.c. electrical potential is measured relative to a stable oxygen reference electrode inserted into the melt stream. The electrical potential measured will be proportional to the amount of hydrogen migration through the platinum wall in the platinum tube sensor. As shown above, the amount of hydrogen migration depends on the relative partial pressure of hydrogen outside versus inside the platinum vessel. Consequently, this measured potential can be used to gauge the relative hydrogen partial pressures outside versus inside the platinum manufacturing vessel. A desired d.c. potential may therefore be maintained by adjusting the relative partial pressures of hydrogen outside versus inside the platinum manufacturing vessel. As explained above, this could be done by enclosing or surrounding portions of the manufacturing process which employ glass contacting platinum, and controlling the humidity or dew point inside these enclosures. Consequently, various combinations could be employed, until a satisfactory hydrogen partial pressure relationship (inside versus outside) is found at which surface blister-free glass was formed. By noting the d.c. potential corresponding to this humidity relationship, the potential could be used as a target potential, and the humidity varied if needed, to maintain the potential at this target potential. Alternatively, one could control the d.c. current to hold the platinum vessel at such a desired constant potential relative to the reference electrode.

A preferred measurement apparatus is shown in FIG. 1. Platinum vessel 10 includes platinum walls 12 through which molten glass 13 is flowing. The platinum walls 12 of vessel 10 can have any shape (e.g. round or rectangular in cross-section), and the direction of flow of the molten glass through vessel 10 is not important. A platinum flag electrode 14 is immersed into the molten glass. By platinum flag, it is meant a flat sheet of platinum, so that the both sides of the platinum contact the molten glass, and therefore the flag does not experience hydrogen permeation. Also immersed into the molten glass 13 is a platinum tube 20, the interior of which is in contact with the atmosphere outside platinum vessel 10. Both flag electrode 14 and the platinum tube 20 are isolated from the platinum manufacturing vessel 10 via an insulating material 24. The flag electrode 14 and platinum tube 20 are then connected as illustrated in FIG. 1. Controller 15 is used to adjust the voltage from variable d.c. power source 16 necessary to maintain the target potential between electrodes 14 and 20. The current necessary to sustain this voltage is then read from ammeter 17 as an indicator of the flow of hydrogen through the platinum wall 20, and thus platinum wall 12 as well. For example, an increase in current indicates a net decrease in the rate of hydrogen migration out of the glass and into the atmosphere outside the Pt system. Conversely, a decrease in current would indicate a net increase in the rate of hydrogen migration out of the glass and into the atmosphere.

The apparatus illustrated in FIG. 1 is enclosed by enclosure 30 (shown schematically), which enables the control of the partial pressure of hydrogen surrounding the platinum vessel 10. Thus, if the measurement system described above indicates a change from the target potential, the humidity inside enclosure 30 can be adjusted to correct for this change. Other variations within the scope of the claimed invention will be apparent to those skilled in the art. For example, the potential between flag 14 and platinum tube 20 could be monitored simply by a voltage regulator, and a signal produced relative to the voltage measured, the signal then being sent to a control device capable of increasing or decreasing the humidity or dew point in the enclosure in response to the signal. In addition, while in FIG. 1, only a portion of the vessel 10 is enclosed, in a preferred embodiment the entire portion of the manufacturing process employing platinum vessels is enclosed. Clearly, a similar control system can be devised if the partial pressure of hydrogen is varied directly.

Although the invention has been described in detail for the purpose of illustration, it is understood that such detail is solely for that purpose and variations can be made therein by those skilled in the art without departing from the spirit and scope of the invention which is defined by the following claims. For example, while many of the principles described herein have been described with respect to platinum manufacturing vessels, these principles are equally applicable to manufacturing vessels employing molybdenum, palladium, rhodium, or alloys thereof.

What is claimed is:

1. A method of forming an oxide glass in a manufacturing process employing a metal selected from the group consisting of platinum, molybdenum, palladium, rhodium, and alloys thereof in a melting, fining, delivery, or forming vessel of the manufacturing process, wherein an interface is present between said vessel and said glass, the method comprising: providing a partial pressure of hydrogen outside the vessel in an amount which is sufficient to prevent formation of oxygen blisters in the region of the glass adjacent said vessel/glass interface.

2. The method of claim 1, wherein said controlling step further comprises adjusting said partial pressure outside in response to the presence of inclusions in the resultant glass.

3. The method of claim 1, wherein said controlling step further comprises controlling the partial pressure of water vapor surrounding the vessel relative to the partial pressure of water vapor inside the vessel.

4. The method of claim 1, further comprising providing an enclosure around the vessel to facilitate said controlling step.

5. The method of claim 4, wherein said controlling step further comprises utilizing a means for manipulating the humidity in said enclosure.

6. The method of claim 4, wherein said controlling step further comprises humidifying said enclosure.

7. The method of claim 4, wherein said controlling step further comprises dehumidifying said enclosure.

8. The method of claim 4, wherein said controlling step further comprises controlling the dew point inside said enclosure.

9. The method of claim 1, wherein said controlling step further comprises monitoring the electric potential in the vessel relative to a reference, and adjusting the partial pressure outside the vessel according to the potential monitored.

10. The method of claim 9, wherein said controlling step further comprises monitoring the DC current required to maintain a desired potential in the vessel relative to said known reference potential.

11. The method of claim 10, wherein said vessel comprises platinum, and the method further comprises increasing the partial pressure of hydrogen outside the vessel in response to a decrease in current, and decreasing the partial pressure of hydrogen outside the vessel in response to an increase in current.

12. The method of claim 10, wherein said vessel comprises molybdenum, and the method further comprises decreasing the partial pressure of hydrogen outside the vessel in response to an increase in current, and increasing the partial pressure of hydrogen outside the vessel in response to a decrease in current.

13. The method of claim 1, further comprising forming said glass using a downdraw glass manufacturing process.

14. The method of claim 1, further comprising selecting batch constituents so that the resultant glass contains less than 0.2 mole percent arsenic expressed as $As_2O_3$.

15. The method of claim 14, further comprising selecting batch constituents so that the β-OH of the resultant glass is below about 0.5/mm.

16. The method of claim 13, wherein said downdraw glass manufacturing process is a sheet forming downdraw process.

17. The method of claim 16, wherein said downdraw process in said melting step is a fusion process.

18. The method of claim 1, further comprising employing a fining agent which consists essentially of an agent selected from the group consisting of $Sb_2O_3$, $CeO_2$, $SnO_2$, $Fe_2O_3$, halide containing compounds, sulfate containing compounds, and mixtures thereof.

19. The method of claim 18, wherein the batch constituents and process control variables are adjusted so that said glass comprises less than 0.1 mole percent $As_2O_3$.

20. The method of claim 18, wherein the batch constituents and process control variables are adjusted so that said glass in said melting step is essentially free of arsenic.

21. The method of claim 1, wherein said melting step comprises employing antimony containing material in an amount which results in the resultant glass having between 0.02 to 1 mole percent $Sb_2O_3$.

22. The method of claim 1, wherein said melting step comprises employing a halide containing compound in an amount sufficient to result in about 0.1 to 2 mole percent halide in the resultant glass.

23. The method of claim 1, wherein the resultant glass comprises an aluminoborosilicate glass, expressed in terms of mole percent on the oxide basis, having:

| | |
|---|---|
| $SiO_2$ | 60–73 |
| $Al_2O_3$ | 8–14 |
| $B_2O_3$ | 5–17 |
| $TiO_2$ | 0–5 |
| $Ta_2O_5$ | 0–5 |
| MgO | 0–5 |
| CaO | 1–13 |
| SrO | 0–8 |
| BaO | 0–14. |

24. The method of claim 23, wherein the resultant glass is essentially free of alkali metal oxides and exhibits a strain point higher than 630° C., and a linear coefficient of thermal expansion over the temperature range 0°–300° C. between 32–46×10$^{-7}$/°C.

25. A method of forming an oxide glass in a manufacturing process employing a metal selected from the group consisting of platinum, molybdenum, palladium, rhodium, and alloys thereof in a melting, fining, delivery, or forming vessel of the manufacturing process, the method comprising:

controlling the partial pressure of hydrogen outside the vessel relative to the partial pressure of hydrogen inside the vessel so that the partial pressure of hydrogen outside the vessel is sufficient to prevent hydrogen migration through the vessel and out of said glass.

* * * * *